(12) United States Patent
    Demou

(10) Patent No.: US 11,058,863 B2
(45) Date of Patent: Jul. 13, 2021

(54) VAD WITH INTRA-HOUSING FLUID ACCESS PORTS

(71) Applicant: HeartWare, Inc., Miami Lakes, FL (US)

(72) Inventor: Zoe N. Demou, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 281 days.

(21) Appl. No.: 16/171,683

(22) Filed: Oct. 26, 2018

(65) Prior Publication Data
    US 2019/0134287 A1    May 9, 2019

Related U.S. Application Data

(60) Provisional application No. 62/581,945, filed on Nov. 6, 2017.

(51) Int. Cl.
    *A61M 60/50*     (2021.01)
    *A61M 60/148*    (2021.01)
    *A61M 60/422*    (2021.01)

(52) U.S. Cl.
    CPC .......... *A61M 60/50* (2021.01); *A61M 60/148* (2021.01); *A61M 60/422* (2021.01); *A61M 2205/0211* (2013.01); *A61M 2205/3303* (2013.01); *A61M 2205/3306* (2013.01); *A61M 2230/207* (2013.01)

(58) Field of Classification Search
    CPC .. A61M 1/1086; A61M 1/1031; A61M 1/122; A61M 2205/0211; A61M 2205/3303; A61M 2205/3306; A61M 2230/207
    USPC ......................................................... 600/17
    See application file for complete search history.

(56) References Cited

U.S. PATENT DOCUMENTS

| 4,796,644 A | 1/1989 | Polaschegg |
| 5,531,789 A * | 7/1996 | Yamazaki ........... A61L 33/0047 600/16 |
| 8,007,254 B2 | 8/2011 | LaRose et al. |
| 9,561,313 B2 | 2/2017 | Taskin |
| 2004/0191116 A1 * | 9/2004 | Jarvik ................... A61M 1/101 422/44 |

(Continued)

FOREIGN PATENT DOCUMENTS

| EP | 0659443 A1 | 12/1994 |
| WO | 0062841 A1 | 10/2000 |
| WO | 0069489 A1 | 11/2000 |

OTHER PUBLICATIONS

International Search Report and Written Opinion dated Jan. 25, 2019, for corresponding International Application No. PCT/US2018/057699; International Filing Date: Oct. 26, 2018 consisting of 12-pages.

*Primary Examiner* — Nadia A Mahmood
(74) *Attorney, Agent, or Firm* — Christopher & Weisberg, P.A.

(57) ABSTRACT

A blood pump including a housing having an inflow tube defining a major axis spanning through the inflow tube and a flow path spanning along the major axis, a rotor disposed within the inflow tube, the rotor and the inflow tube defining a gap therebetween, a stator surrounding the inflow tube and the rotor, and the housing defining an access conduit spanning through the inflow tube and the stator transverse to the major axis, the access conduit being in communication with the gap.

19 Claims, 5 Drawing Sheets

(56) References Cited

U.S. PATENT DOCUMENTS

2009/0149950 A1\* 6/2009 Wampler ............ A61M 1/1022
 623/3.13
2015/0087890 A1 3/2015 Spanier et al.
2015/0335804 A1 11/2015 Marseille et al.

\* cited by examiner

VAD WITH INTRA-HOUSING FLUID ACCESS PORTS

CROSS-REFERENCE TO RELATED APPLICATION

This application claims the benefit of U.S. Application Ser. No. 62/581,945, filed Nov. 6, 2017.

FIELD

The present technology is generally related to a method and system for accessing blood within an implantable blood pump.

BACKGROUND

Mechanical Circulatory Support Devices ("MCSDs") are commonly used to assist the pumping action of a failing heart. Typically, an MCSD includes an implantable blood pump that is surgically implanted in a patient's body. More specifically, the MCSD includes a housing with an inlet, an outlet, and a rotor mounted within the housing. The inlet is connected to a chamber of the patient's heart, typically the left ventricle, whereas the outlet is connected to an artery, such as the aorta. Rotation of the rotor drives blood from the inlet towards the outlet and thus assists blood flow from the chamber of the heart into the artery. The MCSD may be, without limitation, the MVAD® Pump, manufactured by HeartWare, Inc. in Miami Lakes, Fla., USA. The MVAD® Pump is further discussed in U.S. Pat. Nos. 8,007,254 and 9,561,313, the disclosures of which is hereby incorporated in its entirety.

Blood pumps used in MCSDs are desirably provided with contactless bearings so that, in operation, the rotor floats within the housing. With contactless bearings, there is no solid-to-solid contact between the rotor and the housing, and thus no mechanical wear during operation. As a result of the rotor floating within the housing, a gap, such as a radial gap, is generated between the rotor and the housing, which is occupied by fluid, such as blood. In some cases the blood passing through the gap may contain particles of thrombus, a solid or semi-solid deposit generated within a patient's body. Unfortunately, known blood pumps fail to include an access conduit that provides a user with the ability to access the blood within the gap to test the blood for measurements, such as hematocrit, quantification of plasma free hemoglobin, platelet activation, Von Willebrand factor degradation, thrombin generation, and the like. Such testing may be used to analyze the effects of the blood pump's design on the blood. In addition, known bloods pumps do not include access conduits useful for inserting measuring devices through the conduits to measure pressure, temperature, and flow within the housing.

SUMMARY

The techniques of this disclosure generally relate to a method and system for accessing a fluid within a blood pump, the blood pump including a housing defining an access conduit.

In one aspect, the present disclosure provides an implantable blood pump including a housing including an inflow tube defining a major axis spanning through the inflow tube and a flow path spanning along the major axis; a rotor disposed within the inflow tube, the rotor and the inflow tube defining a gap therebetween; a stator surrounding the inflow tube and the rotor; and the housing defining an access conduit spanning through the inflow tube and the stator transverse to the major axis, the access conduit being in communication with the gap.

In another aspect, the disclosure provides the housing including an exterior portion and an interior portion, and the access conduit spans from the exterior portion through the interior portion.

In another aspect, the disclosure provides the stator including a stator core, and the access conduit extends through the stator core.

In another aspect, the disclosure provides a plurality of access conduits extending along the inflow tube and being transverse to the major axis.

In another aspect, the disclosure provides the plurality of access conduits each defining a diameter differing in size with respect to each other.

In another aspect, the disclosure provides the access conduit in fluid communication with a fluid when disposed within the gap, and the fluid includes at least one fluid sample property corresponding to a location of the rotor relative to the inflow tube.

In another aspect, the disclosure provides the access conduit in fluid communication with a fluid when disposed within the inflow tube, and the fluid includes at least one fluid sample property corresponding to a location of the rotor relative to the inflow tube.

In one aspect, the disclosure provides a system for use with an implantable blood pump including the implantable blood pump having a housing including an inflow tube sized to receive a rotor therein, the inflow tube and the rotor defining a gap therebetween when the rotor is within the inflow tube, and the housing defining an access conduit extending through the housing transverse with respect to the inflow tube, the access conduit being in communication with the gap.

In another aspect, the disclosure provides a stator surrounding the inflow tube, and the access conduit spanning through the stator transverse with respect to the inflow tube.

In another aspect, the disclosure provides the stator including a stator core, and the access conduit spans through the stator core transverse with respect to the inflow tube.

In another aspect, the disclosure provides the housing including an exterior portion and an interior portion having the stator therebetween, and the access conduit extends through the exterior portion and the interior portion.

In another aspect, the disclosure provides the housing defining a major axis spanning through the inflow tube and a plurality of access conduits extending along the major axis.

In another aspect, the disclosure provides the plurality of access conduits in communication with the gap when the rotor is disposed within the inflow tube.

In another aspect, the disclosure provides the access conduit in fluid communication with a fluid when disposed within the gap, and the fluid includes at least one fluid sample property corresponding to a location of the rotor relative to the inflow tube.

In another aspect, the disclosure provides the access conduit in fluid communication with a fluid when disposed within the inflow tube, and the fluid includes at least one fluid sample property corresponding to a location of the rotor relative to the inflow tube.

In another aspect, the disclosure provides a fluid transfer device sized to be received within the access conduit.

In another aspect, the disclosure provides a measuring device sized to be received within the access conduit.

In another aspect, the disclosure provides the measuring device as a blood circulation measuring device.

In another aspect, the disclosure provides an imaging device sized to be received within the access conduit.

In one aspect, the present disclosure provides an implantable blood pump including a housing having an exterior portion, an interior portion, and an inflow cannula having an inflow tube extending through the interior portion, and the housing defining a major axis spanning through the inflow tube and a flow path spanning along the major axis; a rotor disposed within the inflow tube, the rotor and the inflow tube defining a gap therebetween; a stator between the exterior portion of the housing and the interior portion of the housing and surrounding the inflow tube and the rotor; and the housing defining an access conduit extending through the inflow tube, the stator, and the exterior portion transverse to the major axis, the access conduit being in communication with the gap.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Before describing in detail exemplary embodiments, it is noted that the embodiments reside primarily in combinations of device components and processing steps related to a method of accessing a fluid within a blood pump. Accordingly, the device and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
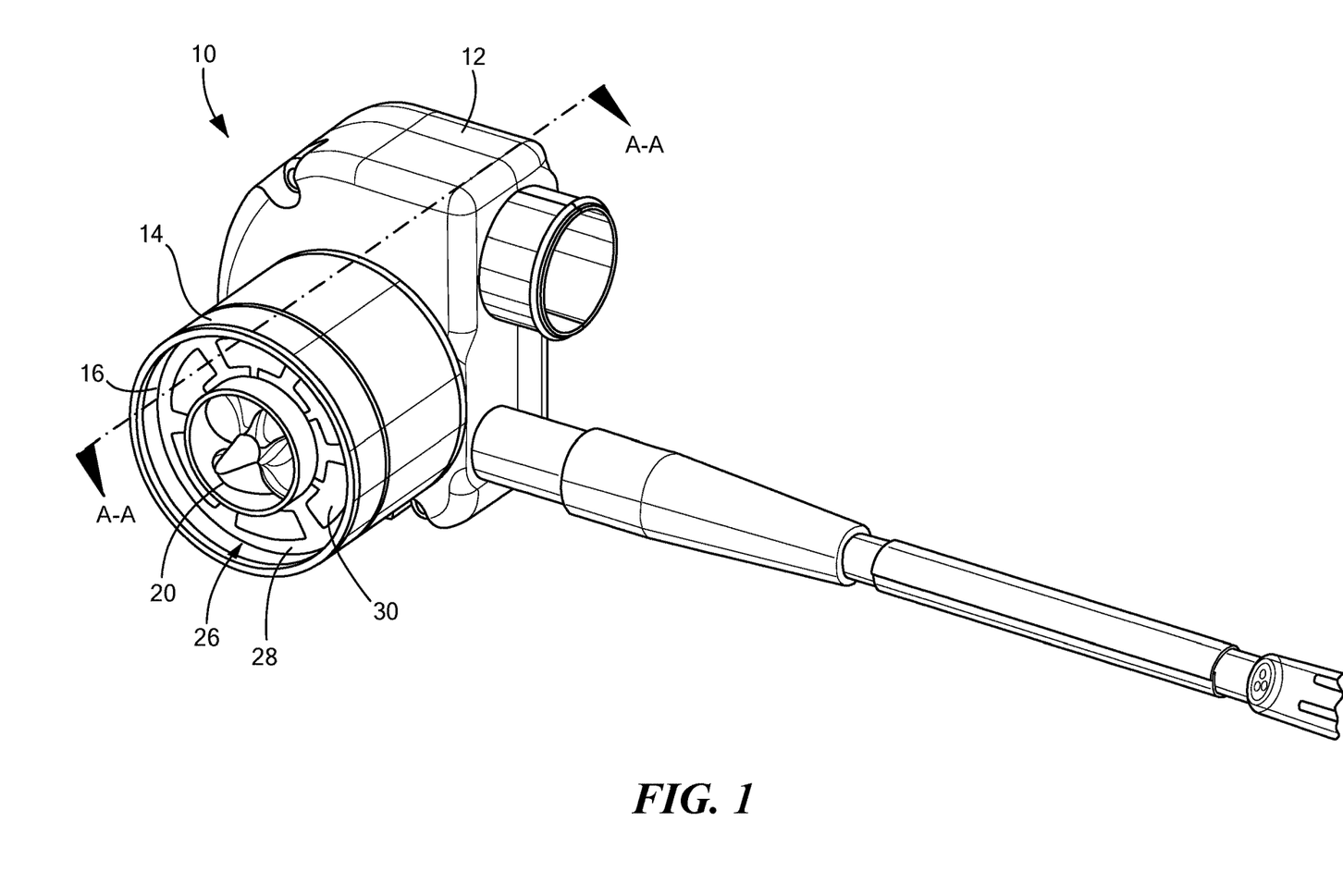
FIG. 1 is a perspective view that illustrates an implantable blood pump.
Figure 2:
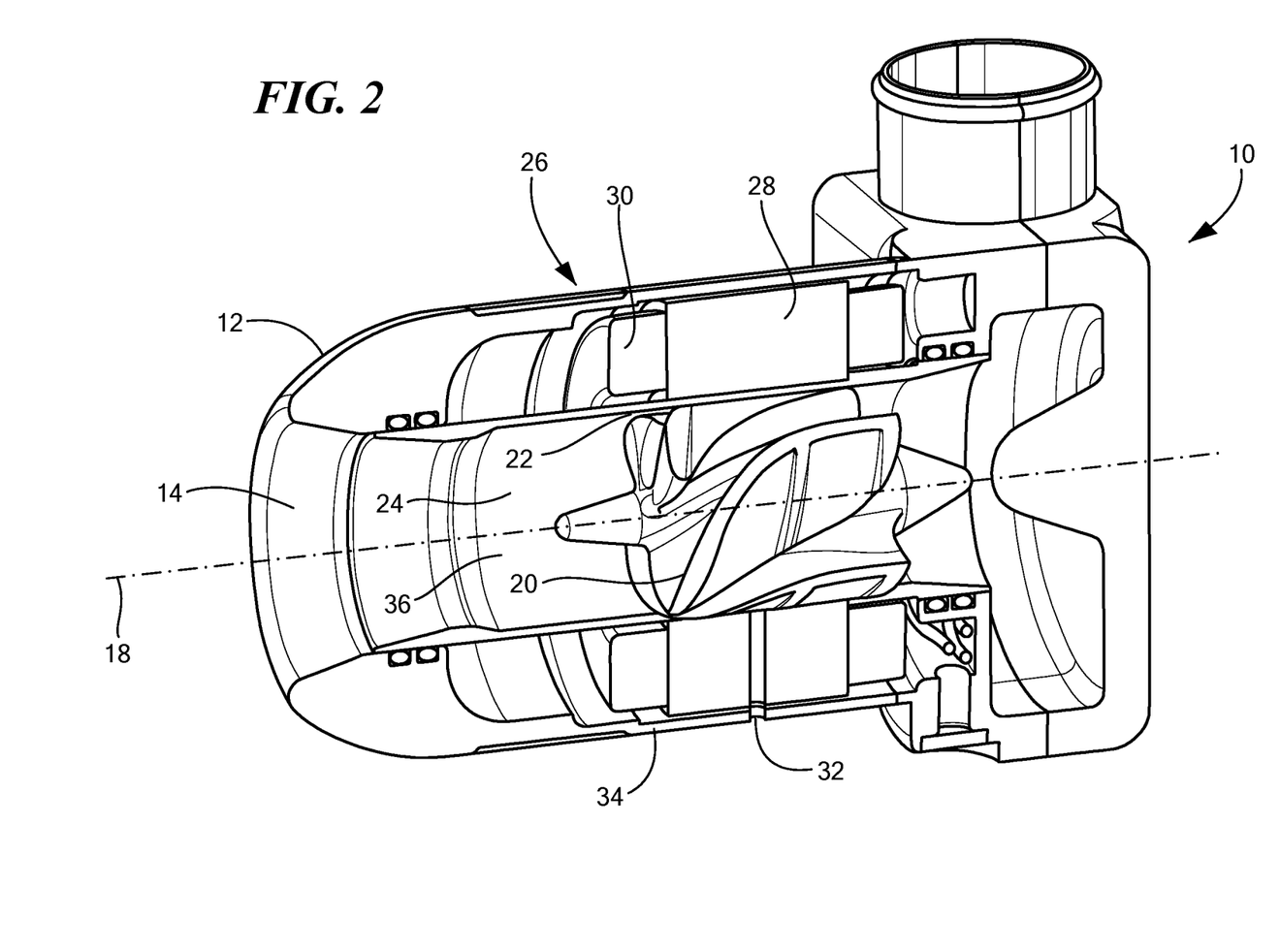
FIG. 2 is a cross-sectional perspective view of the blood pump taken along section A-A of FIG. 1 that illustrates a housing including an exterior portion and an interior portion and defining an access conduit spanning therethrough.

Referring now to the drawings in which like reference designators refer to like elements there is shown in FIGS. 1-2 an exemplary blood pump constructed in accordance with the principles of the present application and designated generally as "10." For example, and without limitation, the blood pump 10 may be the MVAD® Pump. The blood pump 10 is configured to provide a user with bidirectional access to an interior portion of the blood pump to extract a fluid, such as blood, from the pump for analysis associated with blood damage and/or other properties of the blood. In addition, the blood pump 10 is configured to provide the ability to insert devices within the interior portion to measure one or more hemodynamic properties of the blood and/or measure reactions of chemicals acting on the blood and blood components.

As shown in FIG. 1 and the cross-sectional view of the blood pump 10 of FIG. 2 taken along section A-A of FIG. 1, the blood pump 10 may include a housing 12 having an inflow cannula 14 including an inflow tube 16 (FIG. 1), such as a ceramic tube, defining a major axis 18 (FIG. 2) and a flow path spanning through the major axis 18. A rotor 20 may be disposed within the inflow tube 16 such that the rotor 20 and the inflow tube 16 define a gap 22 (FIG. 2), such as a radial gap, therebetween. The term "gap" as used herein is intended to refer to the "radial gap." For example, the gap 22 may be formed between an interior surface 24 of the inflow tube 16 and an outer periphery of the rotor 20.

In one configuration, a stator 26 may be disposed within the housing 12 that surrounds the inflow tube 16 and the rotor 20. The stator 26 is configured to suspend and rotate the rotor 20 when a current is applied to the stator 26. For example, the stator 26 may include a stator core 28 and one or more stator coils 30 configured to receive the current, as is commonly understood by a person of ordinary skill in the art.

With reference to FIG. 2, the housing 12 may define an access port or access conduit 32 spanning from an exterior portion 34 of the housing 12 through the stator 26 and the inflow cannula 14 to an interior portion 36 of the housing 12. The access conduit 32 is configured to allow a fluid, such as blood, to be extracted from the blood pump 10 through the access conduit 32. In one configuration, such as in the MVAD® Pump, the access conduit 32 is transverse to the major axis 18 in fluid communication with the gap 22. As such, blood may be extracted from the gap 22 to determine a range of hematocrit of the blood and a measurement of a level of blood damage and/or other properties of the blood, including hemodynamic properties, as explained in further detail herein. The access conduit 32 is not limited to being transverse to the major axis 18 and may be disposed in alternative configurations, depending on the design of the blood pump 10. When not in use, the access conduit 32 may be sealed using a hemostat, stop cock valve, catheter, or the like.

In one configuration, a method of manufacturing the blood pump 10 may include drilling the access conduit 32 through the housing 12, the stator core 28, and other components, such as backfill, using a mechanical drill or another suitable drilling device. Drilling through the housing 12 and the stator core 28 is performed so as not to impact the performance of the blood pump 10. The method may also include drilling through the inflow tube 16 using a laser so as not to damage the ceramic material. The access conduit 32 may be formed in the individual components of the blood pump 10 prior to assembly of the blood pump 10 or following assembly.

Figure 3:
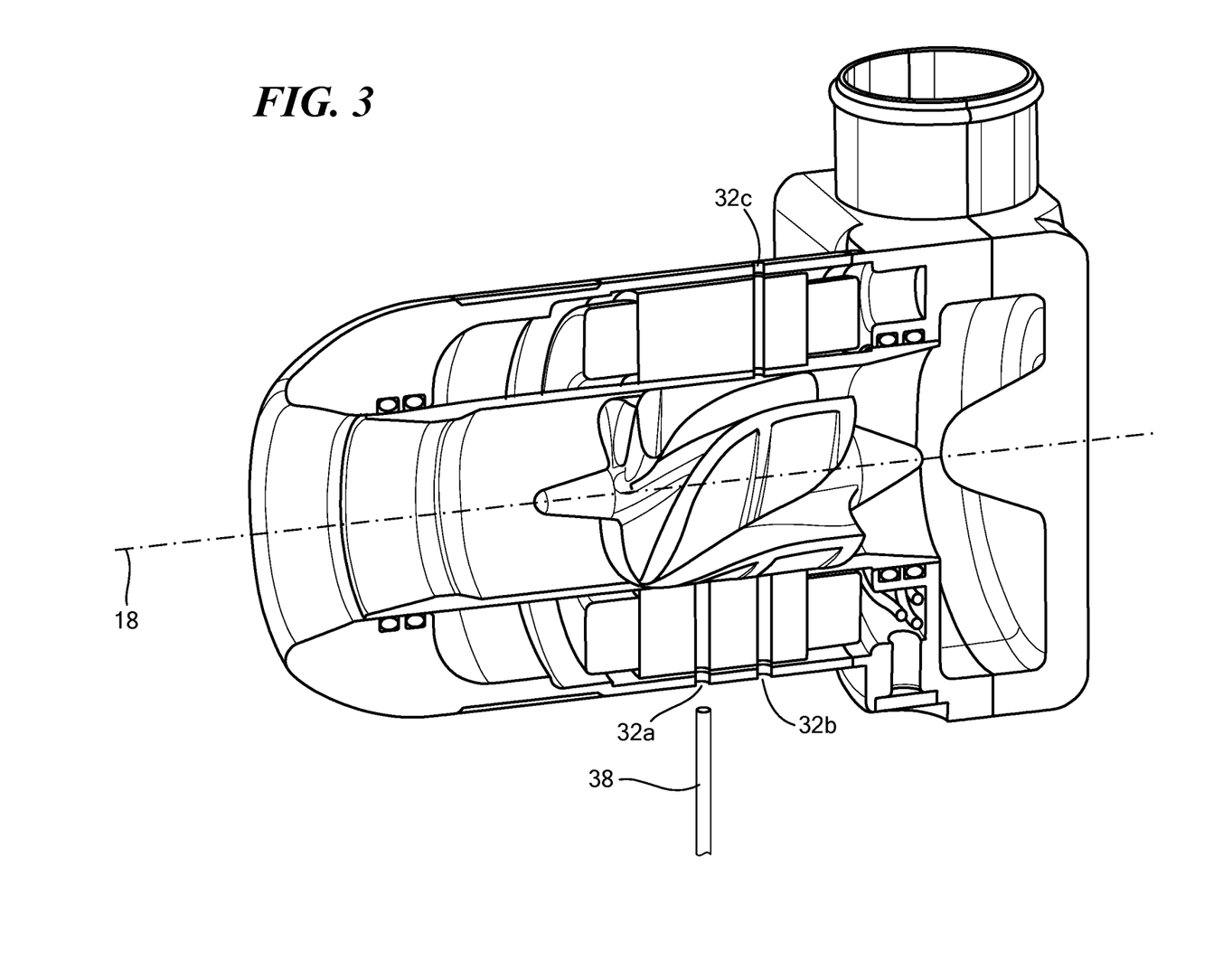
FIG. 3 is a cross-sectional perspective view of the blood pump taken along section A-A of FIG. 1 that illustrates a fluid transfer device insertable through the access conduit of FIG. 3.

With reference now to FIG. 3, the blood pump 10 may include two or more access conduits 32a-32c, such as access conduits 32a and 32b spaced a distance from each other along the major axis 18 of the blood pump 10. The access conduits 32 may also be spaced along an angular direction at generally a same axial position, as shown with the access conduits 32b and 32c and/or different axial positions along the major axis 18, as shown with the access conduits 32a and 32c. For example, as shown in FIG. 3, the blood pump 10 may contain three access conduits 32a-32c, which may be disposed a same distance or various distances from each other along the major axis 18 and the flow path. The number of access conduits 32 and the distance between the access conduits 32 may vary and is not limited to a particular number or distance.

In one configuration, the access conduits 32 may be used in conjunction with a method of accessing a fluid, such as the blood, disposed within the blood pump 10 and particularly within the gap 22. For example, with reference to FIGS. 3-4, the method may include inserting a fluid transfer device 38 through the access conduit 32 and obtaining a fluid sample, such as the blood, from within the gap 22 where the blood is susceptible to damage, such as thrombus. The fluid transfer device 38 may be a stainless-steel needle coupled to a syringe or another instrument having a suitable size and shape for fitting within the access conduit 32 to extract the fluid. The presence of more than one access conduit 32 advantageously allows for backup access conduits 32 for blood to be accessed via one access conduit 32 in the event another access conduit 32 is clogged. Additionally, multiple access conduits 32 enables measurements of differentials of fluid properties along the positional direction of the access conduits 32.

Figure 4:
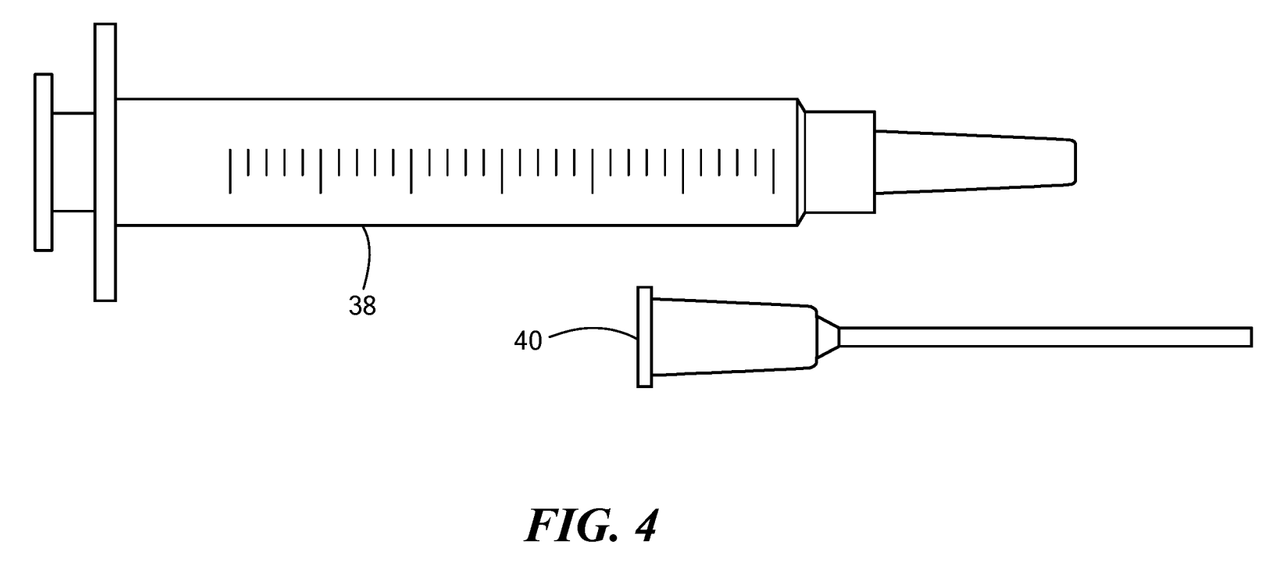
FIG. 4 is a fluid transfer device for coupling to the access conduit.

In one configuration, the access conduits 32 may include a same size diameter for receiving a single size fluid transfer device 38. In the alternative, the diameters of the access conduits 32 may be different dimensions for receiving the fluid transfer devices 38 of different sizes. As shown in FIG. 4, in one non-limiting example, the fluid transfer devices 38 may include needles 40 of at least 16 gauges in size.

In one configuration, the fluid extracted from the gap 22 may be analyzed using various testing and quantification methods to determine a hemodynamic status of the fluid sample alone and/or relative to one or more interior features of the blood pump 10. For example, because blood traveling through the gap 22 may be more susceptible to damage than blood traveling through a remainder of the fluid flow path, the location of the rotor 20 may need to be adjusted as a means of optimizing blood hemolytic performance. In other words, the interior features of the blood pump 10 may be analyzed to adjust a distance of the rotor 20 from the inflow tube 16, which affects the size of the gap 22 and the amount of fluid flow through the blood pump 10. In some instances, the fluid sample alone may be analyzed to determine the overall impact of the blood within the blood pump 10.

In order to compare fluid samples along the major axis 18 and the fluid flow path, one more or fluid samples may be extracted from the access conduits 32. The fluid samples may be analyzed to compare one or more fluid sample properties of the extracted fluid samples. The fluid sample properties may correspond to blood damage, coagulation, thrombogenesis and the like assessed using measurements associated with the quantification of hematocrit, plasma free hemoglobin, platelet activation, Von Willebrand factor degradation, thrombin generation, and the like, and may include the hemodynamic status of the fluid sample. The fluid sample properties may also include quantities pertinent to cell, cellular fragments, cellular products, and/or their associated activation states. As mentioned above, the measurements may be used to determine a percent of the fluid, such as the blood, which travels through the gap 22 in comparison to a percent of the fluid that travels through a remaining portion of the fluid flow path. For example, if the hematocrit of the blood is lower in the gap 22, a determination may be made that a relatively lower percentage of blood cells is traveling through the gap 22 in comparison to the remainder of the flow path. As a result, a relatively low percent of blood cells may be subjected to damage caused by the gap 22 and the hemolytic performance of the pump may be optimized by positioning the rotor 20 accordingly. If the hematocrit of the blood is the same in the gap 22 when compared to the hematocrit in other portions of the fluid flow path, such as along the major axis 18, a determination may be made that a relatively equal amount of red blood cells per unit volume is traveling through the gap 22 and the remainder of the fluid flow path. As such, the location of the rotor 20 relative to the inflow tube 16 may benefit from an adjustment in order for less blood to flow through the gap 22 to decrease the chances of blood damage within the blood pump 10.

The blood within the blood pump 10 and pump performance may benefit from receiving one or more blood treatments, such as medications, depending upon the results of the analysis of the fluid samples. Accordingly, the method may include injecting a blood treatment substance into the access conduit 32 using, for example, the fluid transfer device 38. The blood treatment substance may be a biological substance and/or a chemical substance having a blood treatment component configured to reduce, treat, and/or prevent coagulation, provide one or more anti-platelet therapies, breakdown fibrin in a blood clot, flush the gap 22, and the like.

Figure 5:
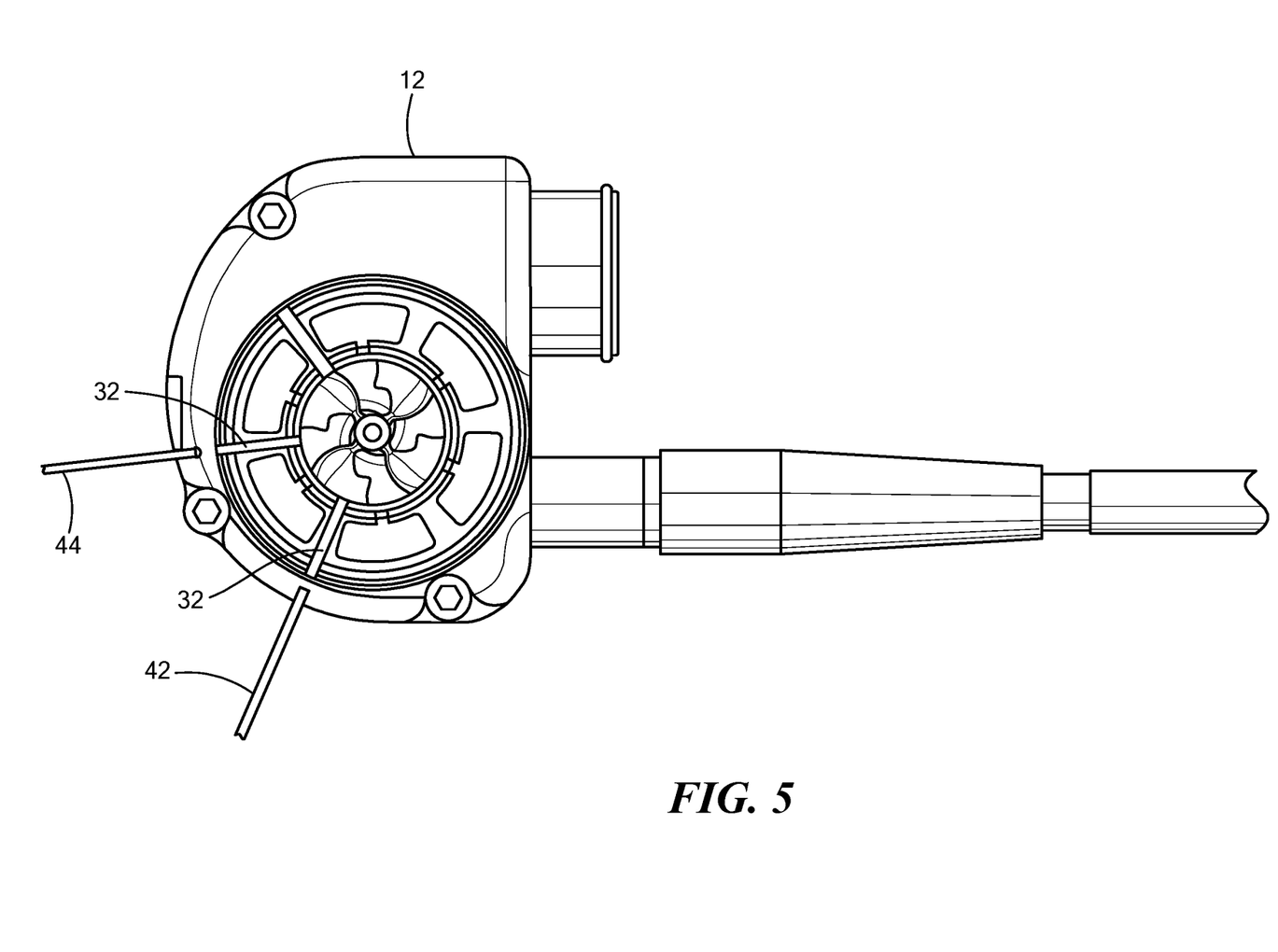
FIG. 5 is a top view that illustrates the blood pump of FIG. 1 and a measuring device coupled to the access conduit.

Referring now to FIG. 5, the method may include inserting a measuring device 42 through the access conduit 32 and analyzing at least one of a pressure measurement, a temperature measurement, and/or a fluid flow measurement within the blood pump housing 12. The measuring device 42 may be a gauge, sensor, or another instrument configured to measure pressure, temperature, and or fluid flow which may affect the mechanics of blood circulation. As such, the measurements may be used to determine an existence of blood damage and/or a modification of a blood count of the fluid sample relative to a threshold blood count which may be obtained prior to use of the blood pump. The modification of the blood count may include changes in red blood cells, white blood cells, platelets, their activation state, cellular products or fragments and the like.

To further analyze the properties of the blood within the blood pump 10, the method may include inserting an imaging device 44 into the access conduit 32 and viewing the fluid sample within the gap 22. The imaging device 44 may be a lens, camera, or the like configured to provide a real time, timelapse or still image of the blood and/or the interior portion 36 of the blood pump 10. The images may be recorded for further analysis particular to a patient and the design of the blood pump.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the disclosure, which is limited only by the following claims.

What is claimed is:

1. An implantable blood pump comprising:
a housing including an inflow tube defining a major axis spanning through the inflow tube and a flow path spanning along the major axis;
a rotor disposed within the inflow tube, the rotor and the inflow tube defining a gap therebetween;
a stator surrounding the inflow tube and the rotor; and
the housing defining an access conduit spanning through the inflow tube and the stator transverse to the major axis, the access conduit being in communication with the gap.

2. The blood pump of claim 1, wherein the housing includes an exterior portion and an interior portion, and the access conduit spans from the exterior portion through the interior portion.

3. The blood pump of claim 1, wherein the stator includes a stator core, and the access conduit extends through the stator core.

4. The blood pump of claim 1, further comprising a plurality of access conduits extending along the inflow tube and being transverse to the major axis.

5. The blood pump of claim 4, wherein the plurality of access conduits each define a diameter differing in size with respect to each other.

6. The blood pump of claim 1, wherein the access conduit is in fluid communication with a fluid when disposed within the gap, and the fluid includes at least one fluid sample property corresponding to a location of the rotor relative to the inflow tube.

7. The blood pump of claim 1, wherein the access conduit is in fluid communication with a fluid when disposed within the inflow tube, and the fluid includes at least one fluid sample property corresponding to a location of the rotor relative to the inflow tube.

8. A system for an implantable blood pump comprising:
the implantable blood pump including a housing having an inflow tube sized to receive a rotor therein, the inflow tube and the rotor defining a gap therebetween when the rotor is within the inflow tube, and the housing defining an access conduit extending through the housing transverse with respect to the inflow tube, the access conduit being in communication with the gap; and
a stator surrounding the inflow tube, and the access conduit spanning through the stator transverse with respect to the inflow tube.

9. The system of claim 8, wherein the stator includes a stator core, and the access conduit spans through the stator core transverse with respect to the inflow tube.

10. The system of claim 8, wherein the housing includes an exterior portion and an interior portion having the stator therebetween, and the access conduit extends through the exterior portion and the interior portion.

11. The system of claim 8, wherein the housing defines a major axis spanning through the inflow tube and a plurality of access conduits extending along the major axis.

12. The system of claim 11, wherein the plurality of access conduits are in communication with the gap when the rotor is disposed within the inflow tube.

13. The system of claim 8, wherein the access conduit is in fluid communication with a fluid when disposed within the gap, and the fluid includes at least one fluid sample property corresponding to a location of the rotor relative to the inflow tube.

14. The system of claim 8, wherein the access conduit is in fluid communication with a fluid when disposed within the inflow tube, and the fluid includes at least one fluid sample property corresponding to a location of the rotor relative to the inflow tube.

15. The system of claim 8, further comprising a fluid transfer device sized to be received within the access conduit.

16. The system of claim 8, further comprising a measuring device sized to be received within the access conduit.

17. The system of claim 16, wherein the measuring device is a blood circulation measuring device.

18. The system of claim 8, further comprising an imaging device sized to be received within the access conduit.

19. An implantable blood pump comprising:
- a housing including an exterior portion, an interior portion, and an inflow cannula having an inflow tube extending through the interior portion, and the housing defining a major axis spanning through the inflow tube and a flow path spanning along the major axis;
- a rotor disposed within the inflow tube, the rotor and the inflow tube defining a gap therebetween;
- a stator between the exterior portion of the housing and the interior portion of the housing and surrounding the inflow tube and the rotor; and
- the housing defining an access conduit extending through the inflow tube, the stator, and the exterior portion transverse to the major axis, the access conduit being in communication with the gap.

\* \* \* \* \*